United States Patent
Irmen et al.

(10) Patent No.: US 11,433,150 B2
(45) Date of Patent: Sep. 6, 2022

(54) AIRCRAFT SANITIZATION SYSTEMS AND DEVICES

(71) Applicant: HCL America, Inc., Sunnyvale, CA (US)

(72) Inventors: Greg Irmen, Laguna Niguel, CA (US); Samaresh Swaro, Sunnyvale, CA (US)

(73) Assignee: HCL America, Inc., Sunnyvale, CA (US)

( * ) Notice: Subject to any disclaimer, the term of this patent is extended or adjusted under 35 U.S.C. 154(b) by 294 days.

(21) Appl. No.: 16/879,935

(22) Filed: May 21, 2020

(65) Prior Publication Data

US 2021/0361791 A1    Nov. 25, 2021

(51) Int. Cl.
*A61L 2/10* (2006.01)
*B64D 11/06* (2006.01)

(52) U.S. Cl.
CPC ............. *A61L 2/10* (2013.01); *B64D 11/062* (2014.12); *A61L 2202/11* (2013.01); *A61L 2202/23* (2013.01); *A61L 2202/25* (2013.01); *A61L 2202/26* (2013.01)

(58) Field of Classification Search
CPC ... A61L 2/10; B64D 11/062; A41D 2400/424; A41F 9/00; A47H 3/12; A44B 11/00; A43C 11/14; B60R 22/00; B60R 21/00; B60R 2022/021; B60N 2/00; B60J 1/2027
See application file for complete search history.

(56) References Cited

U.S. PATENT DOCUMENTS

| | | | |
|---|---|---|---|
| 6,787,782 B1 | 9/2004 | Krosney et al. | |
| 9,550,006 B2 | 1/2017 | Boodaghians et al. | |
| 9,623,133 B2 | 4/2017 | Childress et al. | |
| 9,993,571 B2 | 6/2018 | Lin et al. | |
| 2007/0158499 A1 | 7/2007 | Whittingham | |
| 2012/0273340 A1 | 11/2012 | Felix | |
| 2016/0271289 A1 | 9/2016 | Duffy | |
| 2017/0290935 A1 | 10/2017 | Boodaghians et al. | |
| 2017/0313278 A1* | 11/2017 | Marew | B60R 22/00 |
| 2019/0001015 A1 | 1/2019 | Fiedler et al. | |
| 2019/0021450 A1* | 1/2019 | Chen | A44B 11/2546 |
| 2019/0076558 A1 | 3/2019 | Zhang-Miske et al. | |

FOREIGN PATENT DOCUMENTS

WO    2019068189 A1    4/2019

OTHER PUBLICATIONS

Soojung Lim, Modeling And Design Of A Ultraviolet Disinfection Reactor For Air Recirculation Systems.
Sara E. Beck, UV LED Disinfection 101.

* cited by examiner

*Primary Examiner* — Kevin Joyner
*Assistant Examiner* — Changru Chen
(74) *Attorney, Agent, or Firm* — Kendal Sheets

(57) ABSTRACT

An aircraft sanitization system is disclosed. The aircraft sanitization system includes a frame. The aircraft sanitization system further includes a tray operatively coupled to at least first two corners of the frame and is rotatable about a pivot axis. The tray is configured to be in one of a locked state and an unlocked state based on rotation about the pivot axis. In the unlocked state the tray is at an angle greater than zero with respect to the frame and in the locked state the tray is at an angle equal to zero with respect to the frame. The aircraft sanitization system further includes a set of Ultraviolet (UV) Light Emitting Diodes (LEDs) attached on an exposed surface of the frame, wherein the set of UV LEDs is configured to sanitize the tray when the tray is in the locked state.

6 Claims, 10 Drawing Sheets

AIRCRAFT SANITIZATION SYSTEMS AND DEVICES

TECHNICAL FIELD

This disclosure relates generally to sanitization systems, and more particularly to aircraft sanitization systems and devices.

BACKGROUND

In times of pandemics, monitoring contamination of surfaces due to pathogenic microorganisms (for example, a virus or a bacteria) is of paramount importance. Sanitizing frequently contacted surfaces, such as surfaces within an aircraft, is as necessary as sanitizing body parts to contain a pandemic without disrupting international trade and travels. A pathogenic microorganism may remain active on a surface for days, thus enabling a rapid transmission of infection. By way of an example, a pathogenic microorganism may be Coronavirus, Ebola virus, Nipah virus, *Salmonella typhi*, *Mycobacterium tuberculosis*, or the like. A local outbreak of an epidemic such as COVID-19 may be transmitted nationally or internationally at an increased rate through flight travels. Flight travel is severely restricted in times of such outbreaks, inflicting social and economic damages to countries.

Ultraviolet (UV) light waves in a wavelength range of 100 nano-meter (nm) to 280 nm are germicidal in nature. The germicidal wavelength range of UV corresponds to short-wavelength UV, also known as UV-C. Since development of UV-C Light Emitting Diodes (LEDs), which are inexpensive and energy efficient, UV-C is used in sterilizing surfaces, water, or air.

In the present state of art, techniques for sanitizing surfaces using UV-C light exist. However, the existing techniques do not provide for a holistic sanitization system and are limited to few surfaces and enclosures in an aircraft such as galley, air ducts, aircraft cabin, and lavatory. Further, the techniques require absence of passengers or crew members for sanitization using UV light. However, surfaces such as trays, handles of overhead storage bins, and handles of lavatories are frequently contacted by multiple passengers and crew members during an ongoing flight.

There is, therefore, a need for systems and devices for sanitizing aircraft surfaces in duration of the flight at frequent intervals to contain transmission of pathogenic microorganisms in an aircraft.

SUMMARY

In one embodiment, an aircraft sanitization system is disclosed. In one example, the aircraft sanitization system includes a safety belt comprising a first portion affixed to a first fabric part of the safety belt and a second portion affixed to a second fabric part of the safety belt. The first portion is configured to receive the second portion for fastening the safety belt. The aircraft sanitization system further includes a first stowage encasing configured to completely enclose the first portion. The first stowage encasing includes a first inner wall configured to surround an outer surface of the first portion. The first stowage encasing further includes a first set of Ultraviolet (UV) Light Emitting Diodes (LEDs) affixed to the first inner wall and configured to sanitize the outer surface of the first portion. The first stowage encasing further includes a tongue configured to cooperate with the first portion of the safety belt. The first stowage encasing further includes a second set of UV LEDs attached on a surface of the tongue and configured to sanitize an inner surface of the first portion. The aircraft sanitization system further includes a second stowage encasing configured to enclose the second portion. The second stowage encasing includes a second inner wall configured to surround the second portion. The second stowage encasing further includes a third set of UV LEDs affixed to the second inner wall and configured to sanitize the second portion.

In another embodiment, an aircraft sanitization system is disclosed. In one example, the aircraft sanitization system includes a frame. The aircraft sanitization system further includes a tray operatively coupled to at least first two corners of the frame and is rotatable about a pivot axis. The tray is configured to be in one of a locked state and an unlocked state based on rotation about the pivot axis. In the unlocked state the tray is at an angle greater than zero with respect to the frame and in the locked state the tray is at an angle equal to zero with respect to the frame. The aircraft sanitization system further includes a set of UV LEDs attached on an exposed surface of the frame. The set of UV LEDs is configured to sanitize the tray when the tray is in the locked state.

In yet another embodiment, an aircraft sanitization system is disclosed. The aircraft sanitization system includes an armrest comprising a pocket and a top lid. The pocket is configured to store a tray and the top lid is configured to cover the pocket. The aircraft sanitization system further includes a retractable mechanism enclosed in the pocket. A first end of the retractable mechanism is removably attached to the tray and a second end of retractable mechanism is fixed within the pocket. The retractable mechanism is configured to extract the tray from the pocket in an open state. In the open state the tray is at least partially outside the pocket. The retractable mechanism is further configured to retract the tray into the pocket in a closed state. In the closed state the tray is completely inside the pocket. The aircraft sanitization system further includes a first set of UV LEDs affixed on each inner wall of the pocket. The first set of UV LEDs is configured to sanitize each surface of tray, when the tray is in the closed state.

In another embodiment, an aircraft sanitization device is disclosed. The aircraft sanitization device includes a curved enclosure operatively coupled to a first surface of an enclosed area. At a first position the curved enclosure at least partially encloses a handle affixed to the first surface. The handle enables access to the enclosed area. The curved enclosure further includes an inner surface facing the first surface at the first position of the curved enclosure. The curved enclosure further includes an outer surface facing away from the first surface at the first position. The aircraft sanitization device further includes a set of UV LEDs affixed to the inner surface. The set of UV LEDs is configured to sanitize the handle. The aircraft sanitization device further includes at least one switch placed on at least one of the first surface and a second surface of the enclosed area. Each of the at least one switch is activated in a closed state of the enclosed area and each of the at least one switch is deactivated in an open state of the enclosed area. The aircraft sanitization device further includes at least one locking mechanism. The at least one locking mechanism is configured to engage with the first surface in the closed state. The at least one locking mechanism is further configured to disengage with the first surface in the open state. The aircraft sanitization device further includes a controller communicatively coupled to each of the set of UV LEDs, the at least one switch, and the at least one locking mechanism. The controller is configured to activate the set of UV LEDs, when each of the at least one switch is activated and the locking mechanism engages the first surface in the closed state.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Exemplary embodiments are described with reference to the accompanying drawings. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims. Additional illustrative embodiments are listed below.

Figure 1:
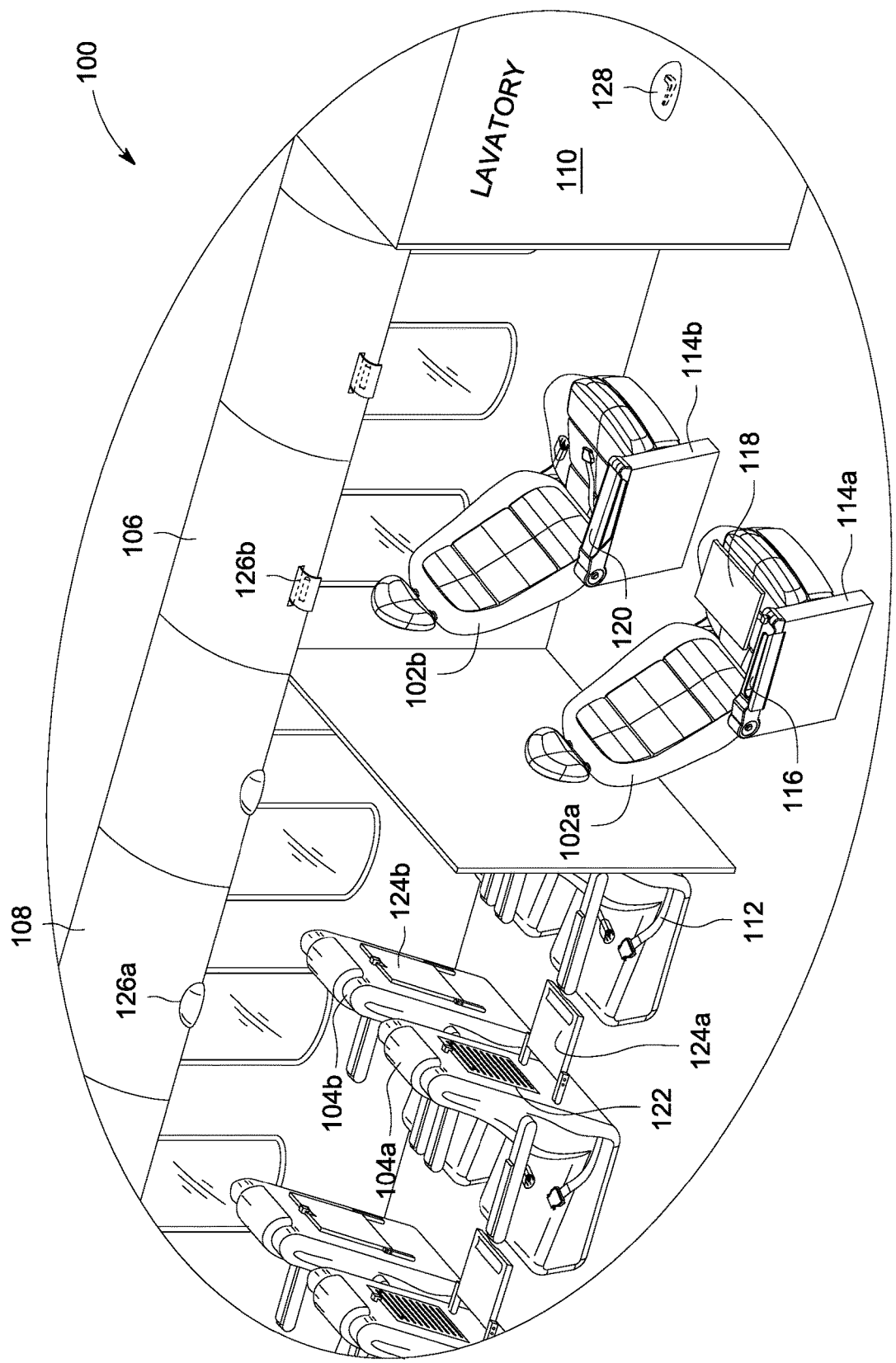
FIG. 1 illustrates an exemplary aircraft cabin where various embodiments may be employed.

In FIG. 1, an exemplary aircraft cabin 100 where various embodiments may be employed, is illustrated. The aircraft cabin 100 may include a plurality of passenger seats (for example, a passenger seat 102a, a passenger seat 102b, a passenger seat 104a, and a passenger seat 104b), a plurality of overhead bins (for example, an overhead bin 106 and an overhead bin 108), and a lavatory 110. Each of the plurality of passenger seats may include a safety belt (for example, a safety belt 112). In an embodiment, the passenger seat 102a may include an armrest 114a and the passenger seat 102b may include an armrest 114b. Further, each of the armrest 114a and the armrest 114b includes a pocket (for example, a pocket 116), a tray (for example, a tray 118), and a top lid (for example, a top lid 120). The pocket may be configured to store the tray and the top lid is configured to cover the pocket, when the tray is enclosed within the pocket. Further, the tray may be in an open state or a closed state. It may be noted that in the open state the tray is at least partially outside the pocket and in the closed state the tray is completely inside the pocket. In the passenger seat 102a, the tray 118 is in an open state, while in the passenger seat 102b, the tray is in the closed state, covered by the top lid 120. This is further explained in detail in conjunction with FIG. 5.

The passenger seat 104a may include a rear surface. A frame (for example, a frame 122) may be affixed to the rear surface. Further, a tray (for example, a tray 124a or a tray 124b) may be operatively coupled to at least first two corners of the frame and the tray as a result is rotatable about a pivot axis (not shown in FIG. 1). The tray may be in an unlocked state, such that, in the unlocked state the tray is at an angle greater than zero with respect to the frame. Alternatively, the tray may be in a locked state, such that, in the locked state the tray is at an angle equal to zero with respect to the frame. In other words, the tray is completely in contact with the frame. Additionally, a latch (not show in FIG. 1) may cooperate or engage with the tray. To this end, the tray may be provided with an indentation, cavity, or a protrusion, which the latch may engage with in the locked state. In the unlocked state, the latch may disengage the tray. The tray 124a is in the unlocked state and the tray 124b is in the locked state. This is further explained in detail in conjunction with FIG. 4.

Each of the passenger seats is also provided with a safety belt, for example, the safety belt 122. The safety belt may include a first portion affixed to a first fabric part of the safety belt and a second portion affixed to a second fabric part of the safety belt. The first portion, for example, may be the female portion of a buckle used to fasten the seat belt. The second portion, for example, may be the male portion of the buckle. Thus, it may be noted that the first portion is configured to receive the second portion for fastening the safety belt. This is further explained in detail conjunction with FIG. 2 and FIG. 3. Further, each of the plurality of overhead bins may include a handle (for example, a handle 126a or a handle 126b). Further, the lavatory 110 may include a handle 128.

As will be appreciated, during a flight, various aircraft surfaces may be contacted by human body parts (for example, fingers, hands, arms, elbows, etc.). By way of an example, the aircraft surfaces may include, but may not be limited to, the safety belt 112, the tray 118, the trays 124a and 124b, the handles 126a and 126b, and the handle 128. It may be noted that the human body parts may be a source of contamination. Communicable diseases may be transmitted through contamination in at least one of the aircraft surfaces. By way of an example, the communicable diseases may include, but are not limited to Coronavirus disease (COVID-19), Ebola virus disease, H1 N1 infection, Nipah virus infection, *Salmonella* infection, tuberculosis, and the like. Therefore, each of the aircraft surfaces may require sanitization at regular intervals even during the duration of the flight.

To achieve this, a plurality of sets of Ultraviolet (UV) Light Emitting Diodes (LEDs) may be affixed at various locations of the aircraft cabin 100. The plurality of sets of UV LEDs may be configured to sanitize each of the aircraft surfaces. As will be appreciated, light in a wavelength range of UV is germicidal. An exposure to UV light for a pre-defined threshold time may sanitize each of the aircraft surfaces. However, the UV light may be required to avoid human contact as UV light is carcinogenic. Thus, sanitization by way of UV light of each of the aircraft surfaces may be performed either in an absence of passengers or crew members on board the aircraft or in isolation from human contact while the aircraft is airborne and operational. This is discussed in detail in conjunction with FIGS. 2-10.

Figure 2:
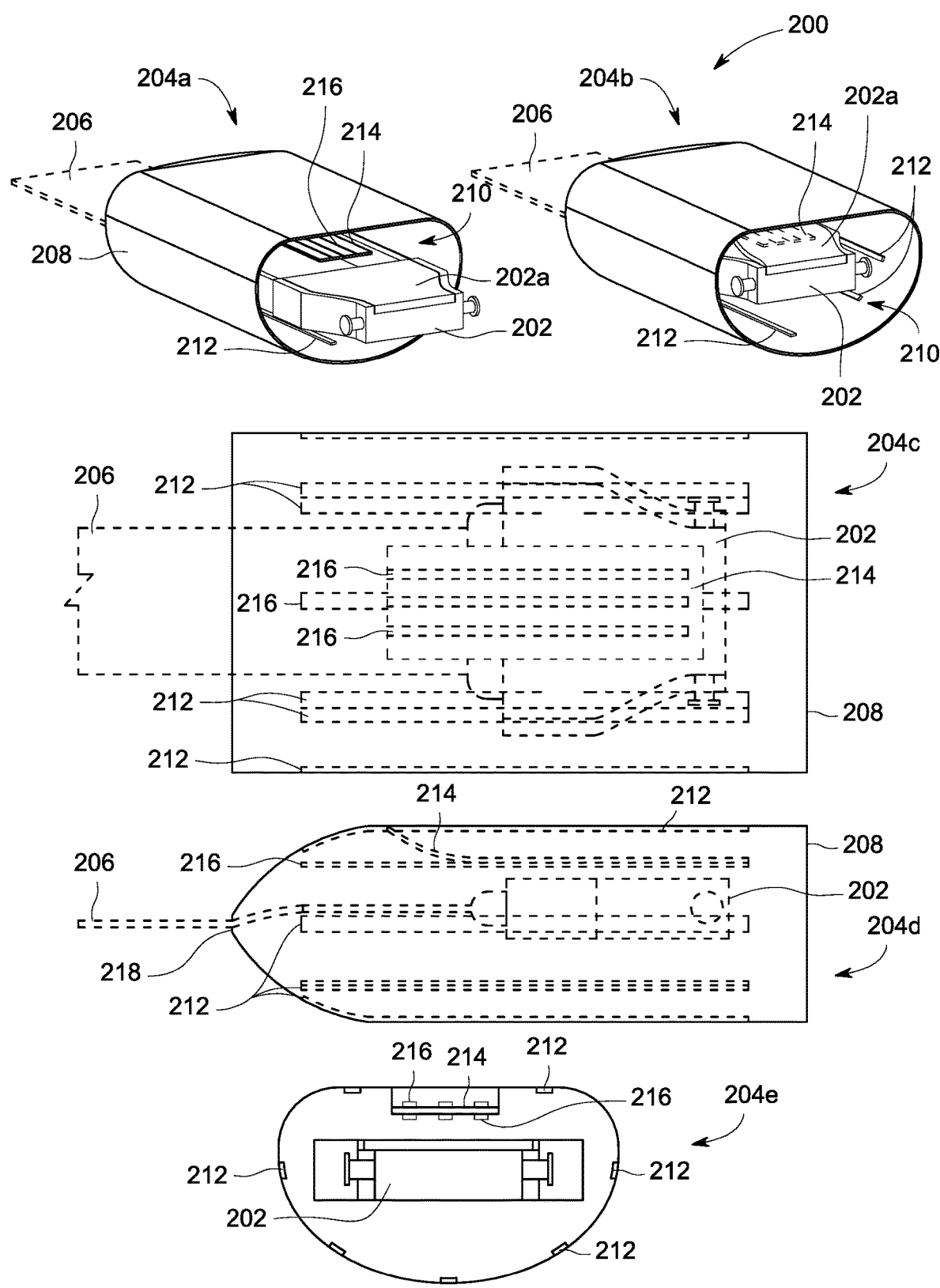
FIG. 2 illustrates multiple views of an aircraft sanitization system for sanitizing a first portion of a safety belt, in accordance with an exemplary embodiment.

Referring now to FIG. 2, multiple views of an aircraft sanitization system 200 for sanitizing a first portion 202 of a safety belt is illustrated, in accordance with an exemplary embodiment. The safety belt may be the safety belt 112 of the aircraft cabin 100. The multiple views of the aircraft sanitization system 200 may include a perspective view 204a, a perspective view 204b, a top view 204c, a side view 204d, and a front view 204e. The aircraft sanitization system 200 may include a first portion 202 (which may be the female portion of a buckle) of a safety belt (for example, the safety belt 112) affixed to a first fabric part 206 of the safety belt. It may be noted that the safety belt may include a second portion (not shown in FIG. 2 and which may be the male part of the buckle) affixed to a second fabric part (not shown in FIG. 2) of the safety belt. The first portion 202 is configured to receive the second portion for fastening the safety belt. The second portion and the second fabric of the safety belt are explained in detail in conjunction with FIG. 3. The perspective view 204a illustrates the first portion 202 and the first fabric part 206 of the safety belt. The aircraft sanitization system 200 may further include a first stowage encasing 208. It may be noted that the first stowage encasing 208 is configured to completely enclose the first portion 202 in order to sanitize it.

The first stowage encasing 208 may include a first inner wall 210, a first set of UV LEDs 212, and a tongue 214. It may be noted that the first inner wall 210 may be configured to surround an outer surface of the first portion 202. Further, the first set of UV LEDs 212 may be affixed to the first inner wall 210. The first set of UV LEDs 212 may be configured to sanitize the outer surface of the first portion 202. In some embodiments, the first set of UV LEDs 212 may include at least one UV-C LED. Further, the tongue 214 may be configured to cooperate with the first portion 202 of the safety belt 112. The perspective view 204b illustrates the cooperation between the tongue 214 and the first portion 202. In the perspective view 204b, it is depicted that upon complete insertion of the first portion 202 inside the first stowage encasing 208, the tongue 214 may lift up a flap 202a of the first portion 202, in order to sanitize an inner wall (not shown in FIG. 2) of the flap 202a and an area of the first portion 202 that is covered by the flap 202a, before being lifted. It may be noted that the tongue 214 may be fixed within the first stowage encasing 208 and may be at least partially inside the first portion 202. In another embodiment, the tongue 214 may be completely inside the first portion 202.

A second set of UV LEDs 216 may be attached on each surface of the tongue 214. The second set of UV-C LEDs 216 is illustrated in the front view 204e. It may be noted that the second set of UV LEDs 216 may be configured to sanitize an inner surface of the first portion 202. In an embodiment, the second set of UV LEDs 216 may sanitize the inner wall (not shown in FIG. 2) of the flap 202a and an area of the first portion 202 that is covered by the flap 202a, before being lifted In some embodiments, the second set of UV LEDs 216 may include at least one UV-C LED. The top view 204c illustrates the first portion 202 enclosed by the first stowage encasing 208. The side view 204d illustrates the cooperation between the tongue 214 and the first portion 202. The front view 204e illustrates the first portion 202 enclosed by the first stowage encasing 208.

In some embodiments, the first stowage encasing 208 includes a first slit 218 (depicted in the side view 204d), which is configured to receive the first fabric part 206. The first slit 218 may include a first pair of rollers (not shown in FIG. 2) that may cooperate with the first fabric part 206. In other words, the first fabric part 206 may pass through the first slit 218 and is then affixed or attached to the first portion 202. It may be noted that the first pair of rollers enable the first stowage encasing 208 to slide over the first fabric part 206 in order to enclose the first portion 202. As discussed earlier, the first fabric part 206 passes through the first stowage encasing 208 via the first slit 218. In an embodiment, the first stowage encasing 208 may include a first motorized mechanism (not shown in FIG. 2) that is coupled to the first pair of rollers. The first motorized mechanism may be configured to activate the first pair of rollers in order to slide the first stowage encasing 208 over the first fabric part 206. The first motorized mechanism, for example, may be an electric motor.

The aircraft sanitization system 200 may further include a first set of sensors (not shown in FIG. 2) within the first stowage encasing 208. It may be noted that the first set of sensors may be configured to determine complete enclosure of the first portion 202 by the first stowage encasing 208. By way of an example, the first set of sensors may include, but may not be limited to a proximity sensor, a camera, an ultrasonic sensor, or the like. Further, the aircraft sanitization system 200 may include a controller (not shown in FIG. 2) that may be communicatively coupled to each of the first set of UV LEDs 212, the second set of UV LEDs 216, the first set of sensors, and the first motorized mechanism.

In response to a sanitization activation signal, the controller may be configured to instruct the first motorized mechanism to slide over the first fabric part 206 to enclose the first stowage encasing 208. The sanitization activation signal, for example, may be generated once the aircraft has been deboarded and no crew or passenger is on-board the aircraft. Alternatively, the sanitization activation signal may be generated when the second portion of the safety belt is not inserted into the first portion 202. In other words, the sanitization activation signal may be generated when the male portion of the safety belt buckle is removed from the female portion of the safety belt buckle.

Additionally, the controller may be configured to activate each of the first set of UV LEDs 212 and the second set of UV LEDs 216 in response to the first set of sensors establishing complete enclosure of the first portion 202 by the first stowage encasing 208. After expiration of a predefined time period since activation of the first set of UV LEDs 212 and the second set of UV LEDs 216, the controller may also be configured to instruct the first motorized mechanism to slide over the first fabric part 206 in order to reveal the first stowage encasing 208. In some embodiments, the controller may be configured to deactivate each of the first set of UV LEDs 212 and the second set of UV LEDs 216 in response to the first set of sensors establishing partial enclosure of the first portion 202 by the first stowage encasing 208. In other words, if someone tries to pull out the first portion 202 currently enclosed by the first stowage encasing 208, the controller may deactivate each of the first set of UV LEDs 212 and the second set of UV LEDs 216. The controller may also be configured to deactivate each of the first set of UV LEDs 212 and the second set of UV LEDs 216 in response to the first set of sensors detecting any motion. It will be apparent to a person skilled in the art that the aircraft sanitization system 200 may not be limited to an aircraft and may be implemented in trains, buses, cars, trucks, or any vehicle thereof. The aircraft sanitization system 200 may also be implemented in public use areas, for example, cinema halls, malls, etc.

Figure 3:
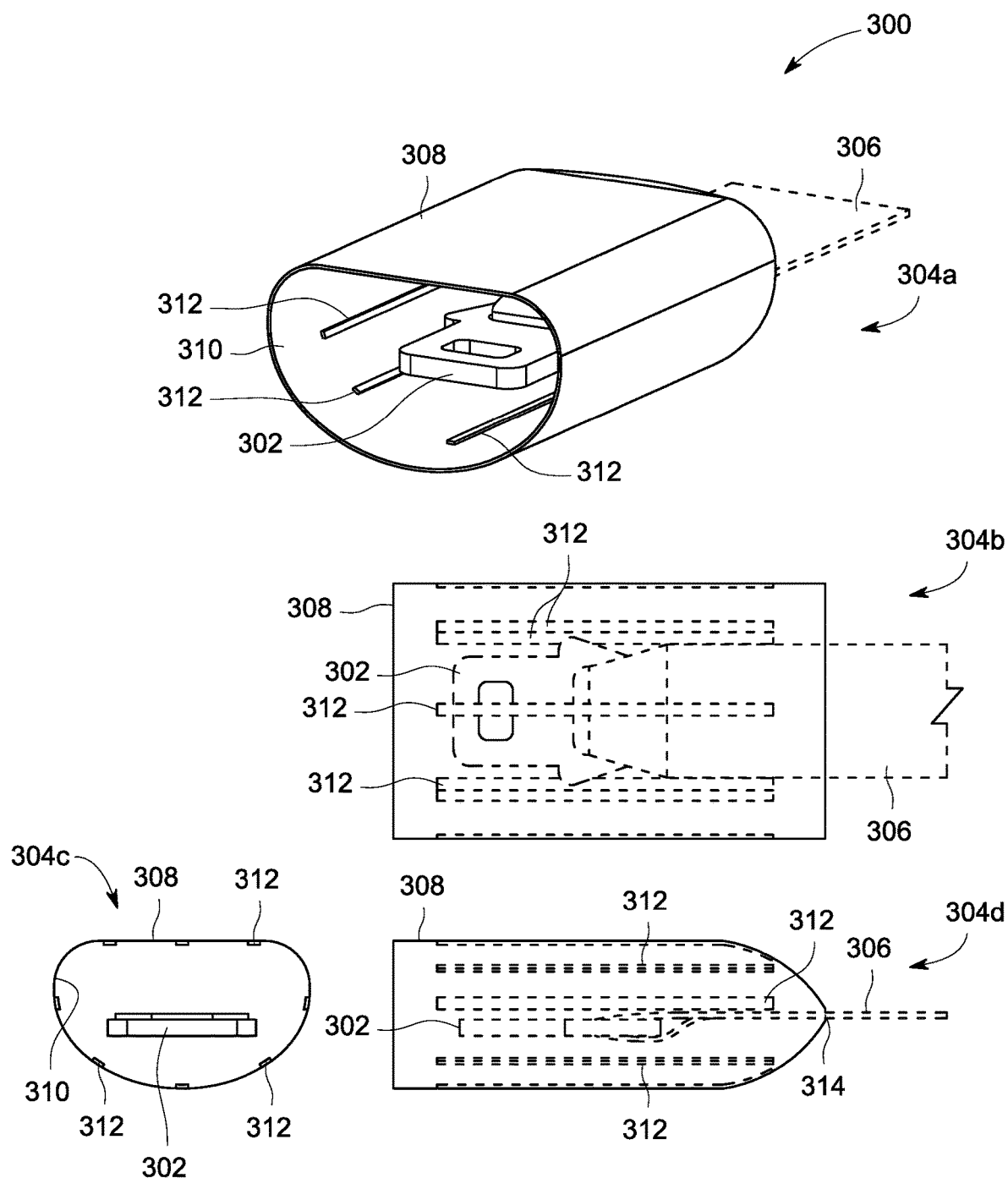
FIG. 3 illustrates multiple views of an aircraft sanitization system for sanitizing a second portion of a safety belt, in accordance with an exemplary embodiment.

Referring now to FIG. 3, multiple views of an aircraft sanitization system 300 for sanitizing a second portion 302 of a safety belt is illustrated, in accordance with an exemplary embodiment. The safety belt may be the safety belt 112 of the aircraft cabin 100. The multiple views of the aircraft sanitization system 300 may include a perspective view 304a, a top view 304b, a front view 304c, and a side view 304d. The perspective view 304a illustrates the second portion 302 affixed to a second fabric part 306 of the safety belt. Further, the aircraft sanitization system 300 may include a second stowage encasing 308 configured to enclose the second portion 302. The second stowage encasing 308 may include a second inner wall 310 and a third set of UV LEDs 312. It may be noted that the second inner wall 310 may be configured to surround the second portion 302. The third set of UV LEDs 312 may be affixed to the second inner wall 310. It may be noted that the third set of UV LEDs 312 is configured to sanitize the second portion 302. In some embodiments, the third set of UV LEDs 312 may include at least one UV-C LED.

In some embodiments, the second stowage encasing 308 includes a second slit 314 (depicted in the side view 304d) configured to receive the second fabric part 306. In other words, the second fabric part 306 passes through the second slit 314 and is affixed to the second portion 302. Further, the second slit 314 may include a second pair of rollers (not shown in FIG. 3) that may cooperate with the second fabric part 306. In other words, the second pair of rollers enable the second stowage encasing 308 to slide over the second fabric part 306 to enclose the second portion 302. The second fabric part 306 passes through the second stowage encasing 308 via the second slit 314. In an embodiment, the second stowage encasing 308 may include a second motorized mechanism (not shown in FIG. 3) that is coupled to the second pair of rollers. The second motorized mechanism may be configured to activate the second pair of rollers in order to slide the second stowage encasing 308 over the second fabric part 306. The second motorized mechanism, for example, may be an electric motor.

The aircraft sanitization system 300 may further include a second set of sensors (not shown in FIG. 3) within the second stowage encasing 308. It may be noted that the second set of sensors may be configured to determine complete enclosure of the second portion 302 by the second stowage encasing 308. By way of an example, the second set of sensors may include, but may not be limited to a proximity sensor, a camera, an ultrasonic sensor, or the like. The aircraft sanitization system 300 may also include a controller (not shown in FIG. 3) that is communicatively coupled to each of the third set of UV LEDs 312, the second set of sensors, and the second motorized mechanism. The controller may be configured to instruct the second motorized mechanism to slide over the second fabric part 306 to enclose the second stowage encasing 308, in response to a sanitization activation signal, which has been discussed in detail in FIG. 2.

Additionally, the controller may be configured to activate the third set of UV LEDs 312 in response to the second set of sensors establishing complete enclosure of the second portion 302 by the second stowage encasing 308. The controller may also be configured to instruct the second motorized mechanism to slide over the second fabric part 306 to reveal the second stowage encasing 308 after expiry of a predefined time period. In some embodiments, the controller may be configured to deactivate the third set of UV LEDs 312 in response to the second set of sensors establishing partial enclosure of the second portion 302 by the second stowage encasing 308. In other words, if someone tries to pull out the second portion 302 currently enclosed by the second stowage encasing 308, the controller may deactivate the third set of UV LEDs 312. The controller may also be configured to deactivate the third set of UV LEDs 312 in response to the second set of sensors detecting any motion. It will be apparent to a person skilled in the art that the aircraft sanitization system 300 may not be limited to an aircraft and may be implemented in trains, buses, cars, trucks, or any vehicle thereof. The aircraft sanitization system 300 may also be implemented in public use areas, for example, cinema halls, malls, etc.

Figure 4:
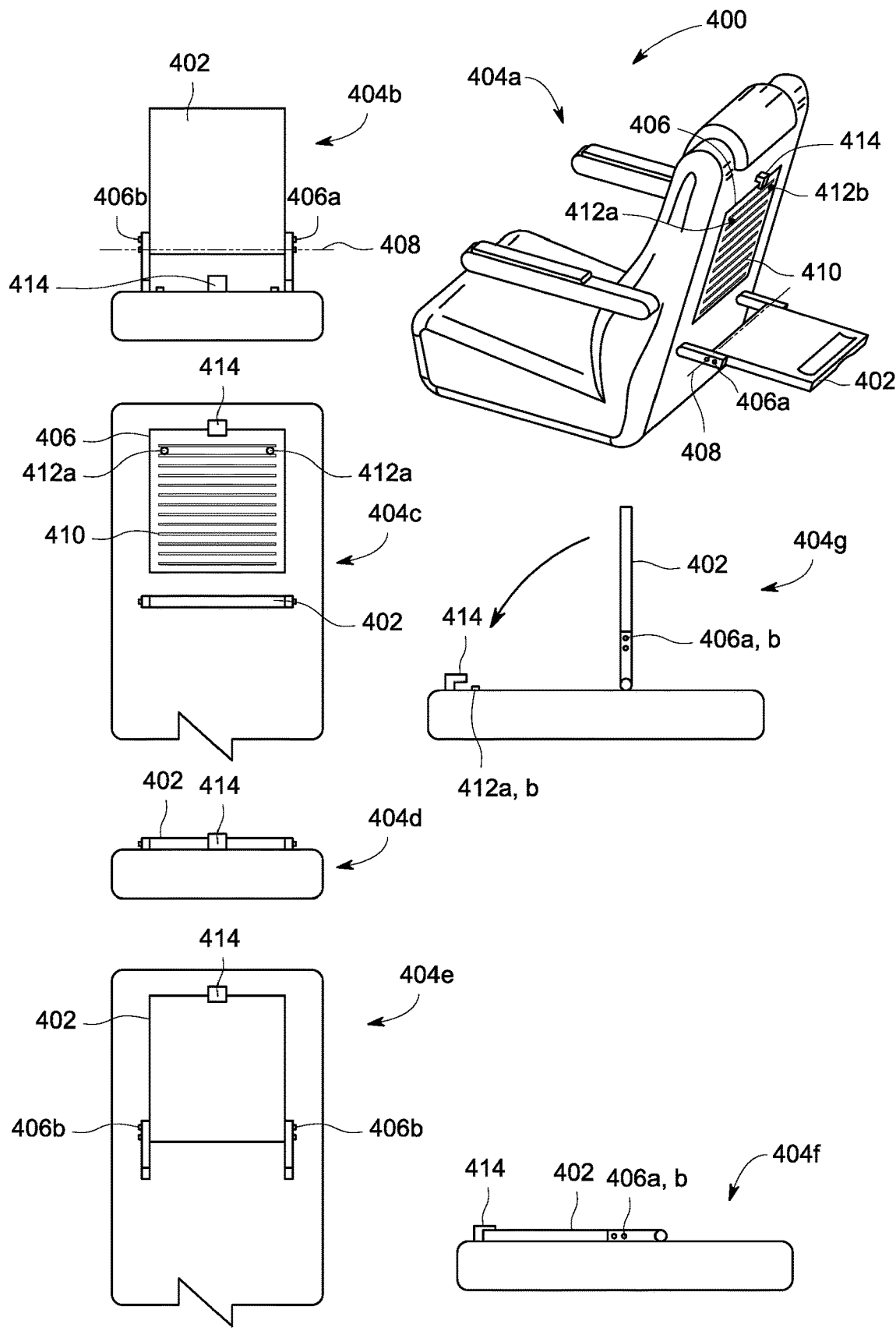
FIG. 4 illustrates multiple views of an aircraft sanitization system for sanitizing a tray, in accordance with an exemplary embodiment.

Referring now to FIG. 4, multiple views of an exemplary aircraft sanitization system 400 for sanitizing a tray 402 is illustrated, in accordance with an exemplary embodiment. The multiple views of the aircraft sanitization system 400 may include a perspective view 404a, a top view 404b, a front view 404c, a top view 404d, a front view 404e, a closed side view 404f, and an open side view 404g. The aircraft sanitization system 400 may include a frame 406 and the tray 402. In an embodiment, the frame 406 may be affixed on a rear surface of a passenger seat (for example, the passenger seat 104a) in the aircraft cabin 100. In another embodiment, the frame may be affixed to a wall of the aircraft cabin.

The tray 402 may be operatively coupled to at least first two corners (for example, corners 406a and 406b) of the frame 406 and may be rotatable about a pivot axis 408 (that crosses the corners 406a and 406b). It may be noted that the tray 402 may be configured to be in a locked state and/or an unlocked state based on rotation about the pivot axis 408. It may also be noted that in the unlocked state, the tray 402 is at an angle greater than zero with respect to the frame 406 and in the locked state, the tray 402 is at an angle equal to zero with respect to the frame 406. The tray 402 is illustrated in the unlocked state in each of the top view 404d, the front view 404e, and the side view 404f. The tray 402 is illustrated in the unlocked state in each of the perspective view 404a, the top view 404b, the front view 404c, and the side view 404g.

The aircraft sanitization system 400 may further include a set of UV LEDs 410 attached on an exposed surface of the frame 402. The tray 402, in the locked state, may be facing the exposed surface of the frame 402. It may be noted that the set of UV LEDs 410 may be configured to sanitize the tray 402 when the tray 402 is in the locked state. In some embodiments, the set of UV LEDs 410 may include at least one UV-C LED. The frame 406 may include at least one switch (for example, a switch 412a and a switch 412b) located on an outer periphery of the frame 406. It may be noted that in the locked state, the tray 402 encloses and activates each of the at least one switch. The frame 406 may also include a latch 414 that may cooperate with the tray 402. It may be noted that in the locked state the latch 414 may engage with the tray 402 and in the unlocked state the latch 414 may disengage the tray 402. To this end, the tray 402 may be provided with an indentation, cavity, or a protrusion, which the latch 414 may engage with in the locked state.

The frame 406 may include a controller that may be communicatively coupled to the at least one switch and the latch 414. The controller may activate the set of UV LEDs 410, when a set of conditions are met. It may be noted that the set of conditions may include each of the tray 402 being in the locked state, the at least one switch being activated, and the latch 414 engaging the tray 402. In some embodiments, the frame 406 may also include at least one sensor that may be configured to generate a deactivation signal based on a predefined criterion. By way of an example, the predefined criterion may be transition of the tray 402 from the locked state to the unlocked state. By way of another example, the predefined criterion may be detection of motion or a body part of a human. The controller may be communicatively coupled to the least one sensor. The controller may thus be configured to deactivate the set of UV LEDs 410 in response to the deactivation signal generated by the at least one sensor. It may be noted that the at least one sensor may be located at the outer periphery of the frame 406 and may be enclosed by the tray 402 in the locked state. It will be apparent to a person skilled in the art that the aircraft sanitization system 400 may not be limited to an aircraft and may be implemented in trains, buses, cars, trucks, or any vehicle thereof. The aircraft sanitization system 400 may also be implemented in public use areas, for example, cinema halls, malls, etc.

Figure 5:
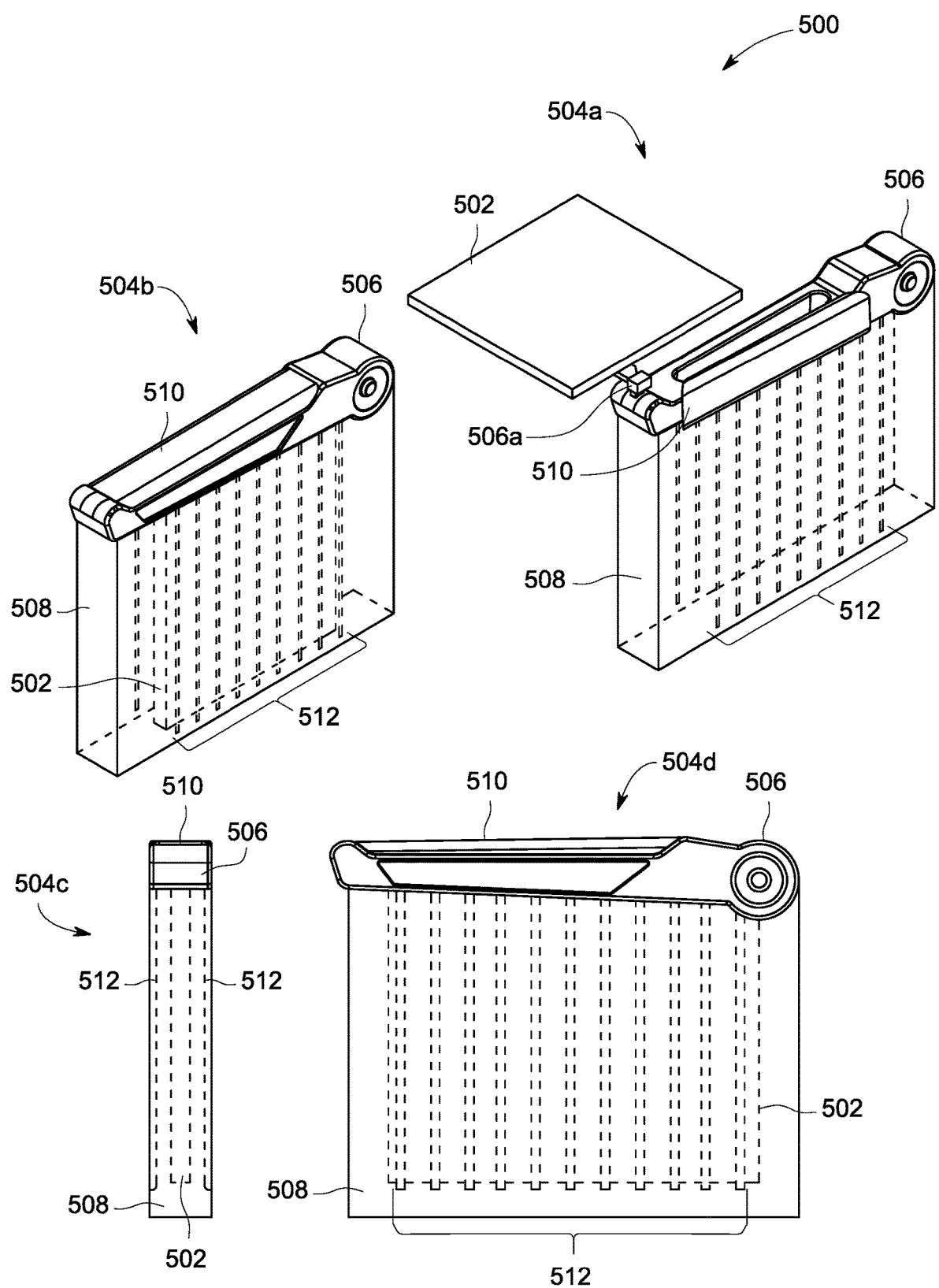
FIG. 5 illustrates multiple views of an aircraft sanitization system for sanitizing a tray, in accordance with an exemplary embodiment.

Referring now to FIG. 5, multiple views of an aircraft sanitization system 500 for sanitizing a tray 502 is illustrated, in accordance with another embodiment. in the multiple views include a perspective view 504a, a perspective view 504b, a front view 504c, and a side view 504d. The aircraft sanitization system 500 may include an armrest 506 of a passenger seat. By way of an example, the passenger seat may be the passenger seat 102a of the aircraft cabin 100. The armrest 506 may include a pocket 508 and a top lid 510. It may be noted that the pocket 508 may be configured to store the tray 502. It may also be noted that the top lid 510 may be configured to cover the pocket 508 once the tray 502 is enclosed within the pocket 508. Further, the aircraft sanitization system 500 may include a retractable mechanism 506a that is enclosed in the pocket 508. It may be noted that a first end (not shown in FIG. 5) of the retractable mechanism 506a is removably attached to the tray 502 and a second end (not shown in FIG. 5) of retractable mechanism is fixed within the pocket 508. The retractable mechanism 506a may be configured to extract the tray 502 from the pocket 508 in an open state. It may be noted that in the open state the tray 502 may be at least partially outside the pocket 508. Additionally, the retractable mechanism 506a may be configured to retract the tray 502 into the pocket 508 in a closed state. It may be noted that in the closed state the tray 502 may be completely inside the pocket 508. The tray 502 is illustrated in an open state in the perspective view 504a and in a closed state in the perspective view 504b.

Further, the aircraft sanitization system 500 may include a first set of UV LEDs 512 affixed on each inner wall of the pocket 508. The first set of UV LEDs 512 may be configured to sanitize each surface of tray 502, when the tray 502 is in the closed state. In some embodiments, the first set of UV LEDs 512 may include at least one UV-C LED. In an embodiment, a first end (not shown in FIG. 5) of the top lid 510 may be hinged to the armrest 506 to enable rotation of the top lid 510 about a pivot axis and a second end (not shown in FIG. 5) of the top lid 510 may cooperate with the armrest 506 to enable the closed state and the open state. Further, the aircraft sanitization system 500 may include at least one switch (not shown in FIG. 5) located on the armrest 506. It may be noted that each of the at least one switch is configured to be enclosed and activated by the top lid 510 in the closed state. Additionally, each of the at least one switch is configured to be disclosed and deactivated by the top lid 510 in the open state.

The aircraft sanitization system 500 may further include a locking mechanism (not shown in FIG. 5). It may be noted that the locking mechanism may be configured to cooperate with the second end of the top lid 510 to enable the closed state and the open state. The locking mechanism may engage with the top lid 510 in the closed state and may disengage with the top lid 510 in the open state. Further, the aircraft sanitization system 500 may include a controller (not shown in FIG. 5) that may be communicatively coupled to each of the at least one switch and the locking mechanism. It may be noted that the controller may be configured to activate the first set of UV LEDs 512, when each of the at least one switch is activated and the locking mechanism engages the top lid 510 in the closed state.

In an embodiment, the aircraft sanitization system 500 may include at least one sensor configured to generate a deactivation signal in response to a predefined criterion. By way of an example, the predefined criterion may be transition of the tray 502 from the locked state to the unlocked state. By way of another example, the predefined criterion may be detection of motion or a body part of a human. The controller may be communicatively coupled to the at least one sensor. It may be noted that the controller may further be configured to deactivate the first set of UV LEDs 512 in response to the deactivation signal generated by the at least one sensor. It will be apparent to a person skilled in the art that the aircraft sanitization system 500 may not be limited to an aircraft and may be implemented in trains, buses, cars, trucks, or any vehicle thereof. The aircraft sanitization system 500 may also be implemented in public use areas, for example, cinema halls, malls, etc.

Figure 6:
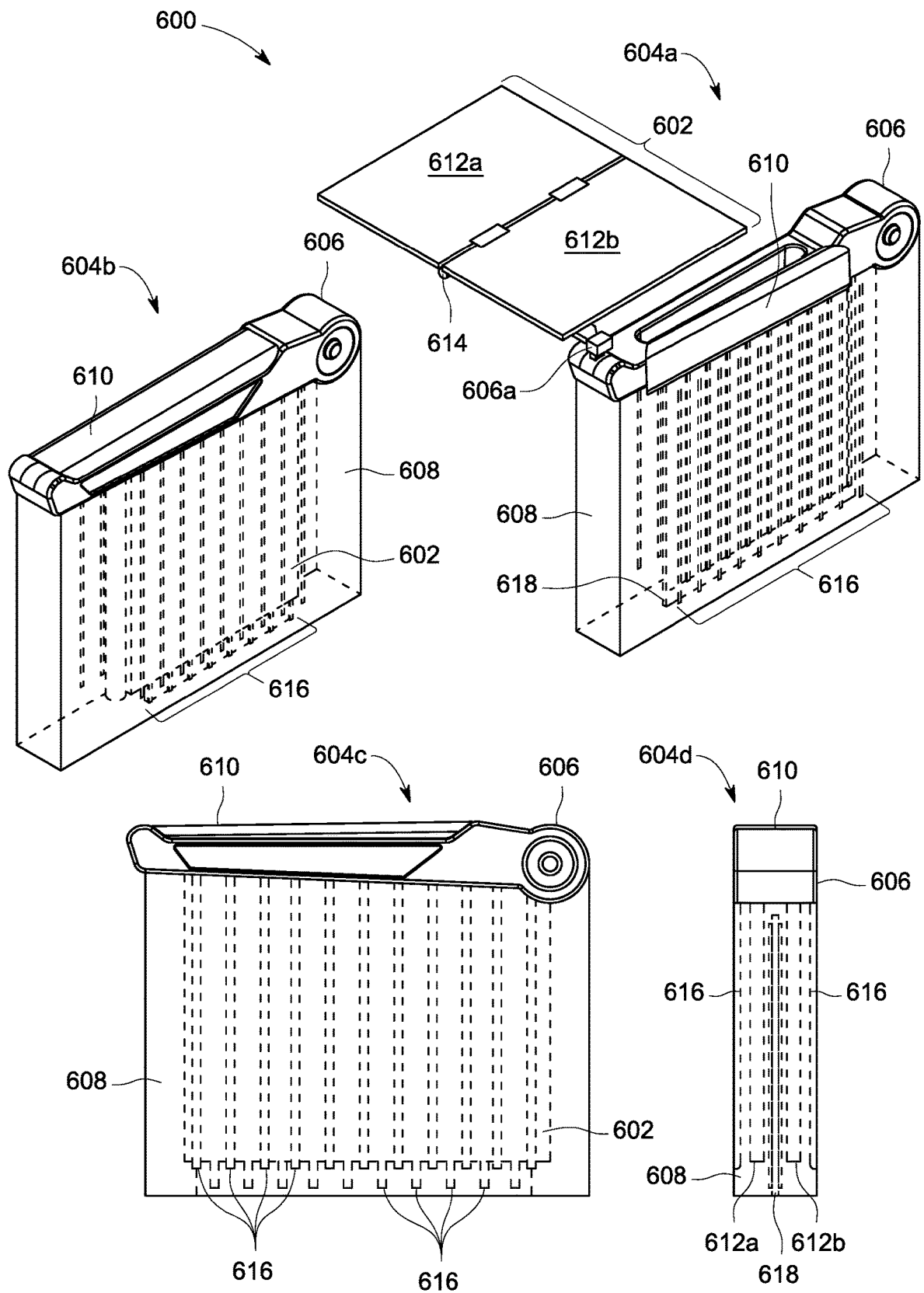
FIG. 6 illustrates multiple views of an aircraft sanitization system for sanitizing a foldable tray, in accordance with an exemplary embodiment.

Referring now to FIG. 6, multiple views of an aircraft sanitization system 600 for sanitizing a foldable tray 602 is illustrated, in accordance with an exemplary embodiment. The multiple views include a perspective view 604a, a perspective view 604b, a front view 604c, and a side view 604d. The aircraft sanitization system 600 may include an armrest 606 of a passenger seat. The passenger seat may be the passenger seat 102a of the aircraft cabin 100. The armrest 606 may include a pocket 608 and a top lid 610. It may be noted that the pocket 608 may be configured to store the foldable tray 602. It may also be noted that the top lid 610 may be configured to cover the pocket 608. The foldable tray 602 may include a plurality of portions (for example, a portion 612a and a portion 612b) hinged to each other. Additionally, at least one of the plurality of portions may be foldable around an associated pivot axis 614 over the remaining plurality of portions. Further, the aircraft sanitization system 600 may include a retractable mechanism 606a enclosed in the pocket 608. It may be noted that a first end (not shown in FIG. 6) of the retractable mechanism 606a may be removably attached to the foldable tray 602 and a second end of retractable mechanism 606a (not shown in FIG. 6) may be fixed within the pocket 608. The retractable mechanism 606a may be configured to extract the foldable tray 602 from the pocket 608 in an open state. It may be noted that in the open state the foldable tray 602 may be at least partially outside the pocket 608. Additionally, the retractable mechanism 606a may be configured to retract the foldable tray 602 into the pocket 608 in a closed state. It may be noted that in the closed state the foldable tray 602 may be completely inside the pocket 608. The foldable tray 602 is illustrated in an open state in the perspective view 604a and in a closed state in the perspective view 604b.

The aircraft sanitization system 600 may further include a first set of UV LEDs 616 affixed on each inner wall of the pocket 608. The first set of UV LEDs 616 may be configured to sanitize each surface of the foldable tray 602, when the foldable tray 602 is in the closed state. In some embodiments, the first set of UV LEDs 616 may include at least one UV-C LED. In an embodiment, a first end (not shown in FIG. 6) of the top lid 610 may be hinged to the armrest 606 to enable rotation of the top lid 610 about a pivot axis and a second end (not shown in FIG. 6) of the top lid 610 may cooperate with the armrest 606 to enable the closed state and the open state. Further, the aircraft sanitization system 600 may include at least one switch (not shown in FIG. 6) located on the armrest 606. It may be noted that each of the at least one switch may be configured to be enclosed and activated by the top lid 610 in the closed state. Additionally, each of the at least one switch may be configured to be disclosed and deactivated by the top lid 610 in the open state.

Further, the pocket 608 may include at least one tongue (for example, a tongue 618) located between inner walls of the pocket 608. A second set of UV LEDs (not shown in FIG. 6) may be attached to each face of the at least one tongue. It may be noted that the second set of UV LEDs may be configured to sanitize at least one of the plurality of portions of the foldable tray 602. By way of an example, the portion 612a may be foldable around the pivot axis 614 over the portion 612b, such that, when the foldable tray 602 may be in a closed state, the foldable tray 602 may be completely inside the pocket 608 and the portion 612a may be folded over such that an angle formed by each of edges of the portion 612a with a corresponding edge of the portion 612b may be a zero angle. Further, in the closed state, the tongue 618 may be located between the portion 612a and the portion 612b. The second set of UV LEDs may be attached on each face of the tongue 618 and may be configured to sanitize a surface of each of the portion 612a and the portion 612b of the foldable tray 602.

The aircraft sanitization system 600 may include a locking mechanism (not shown in FIG. 6). It may be noted that the locking mechanism may be configured to cooperate with the second end of the top lid 610 to enable the closed state and the open state. The locking mechanism may engage with the top lid 610 in the closed state and may disengage with the top lid 610 in the open state. Further, the aircraft sanitization system 600 may include a controller that may be communicatively coupled to each of the at least one switch and the locking mechanism. It may be noted that the controller may be configured to activate the first set of UV LEDs 616 and the second set of UV LEDs, when each of the at least one switch is activated and the locking mechanism engages the top lid 610 in the closed state. In an embodiment, the aircraft sanitization system 600 may include at least one sensor configured to generate a deactivation signal in response to a predefined criterion. By way of an example, the predefined criterion may be transition of the foldable tray 602 from the locked state to the unlocked state. By way of another example, the predefined criterion may be detection of motion or a body part of a human. The controller may be communicatively coupled to the at least one sensor. It may be noted that the controller may further be configured to deactivate the first set of UV LEDs 616 and the second set of UV LEDs in response to the deactivation signal generated by the at least one sensor. It will be apparent to a person skilled in the art that the aircraft sanitization system 600 may not be limited to an aircraft and may be implemented in trains, buses, cars, trucks, or any vehicle thereof. The aircraft sanitization system 600 may also be implemented in public use areas, for example, cinema halls, malls, etc.

Figure 7:
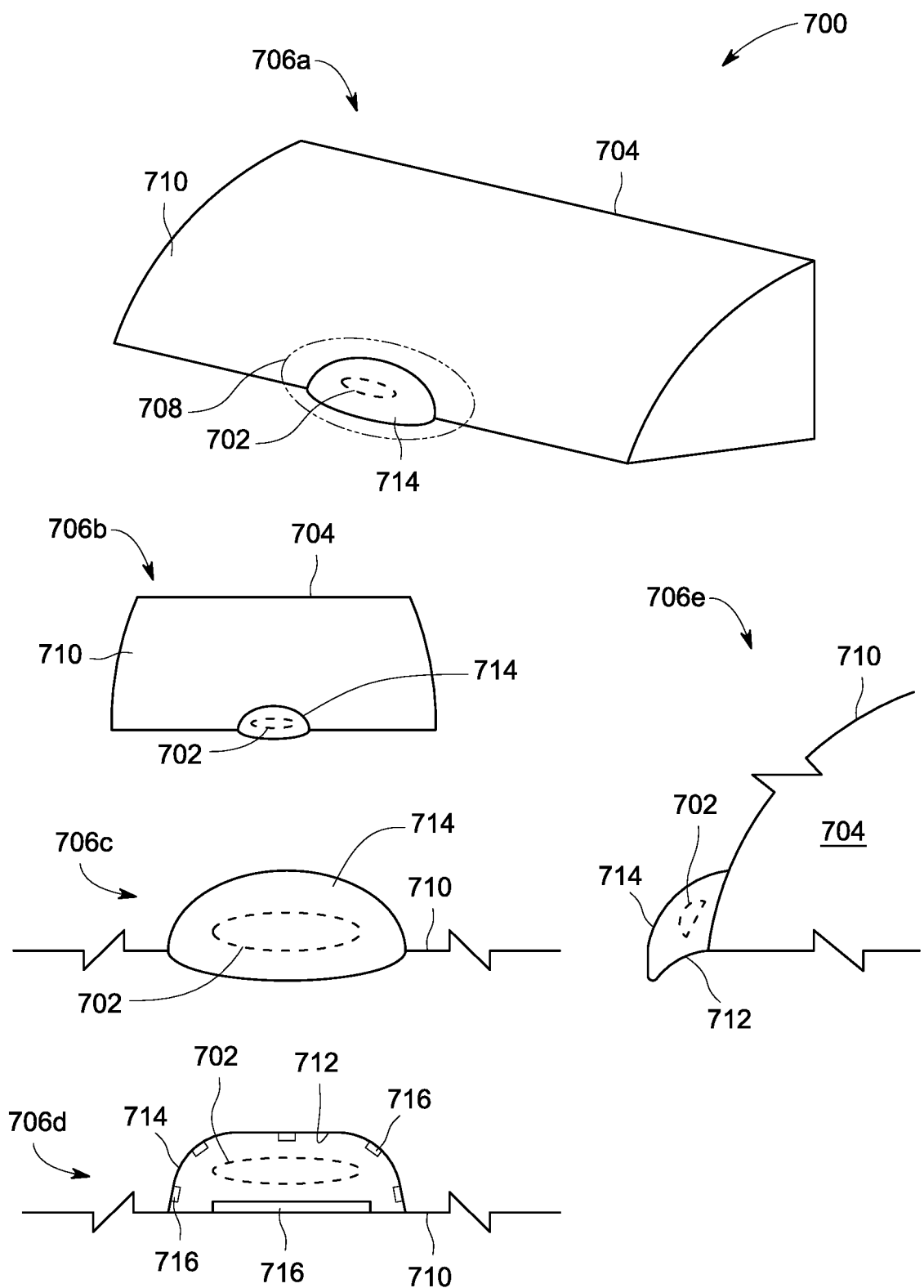
FIG. 7 illustrates multiple views of an aircraft sanitization device for sanitizing a handle of an overhead storage bin, in accordance with an exemplary embodiment.

Referring now to FIG. 7, multiple views of an aircraft sanitization device 700 for sanitizing a handle 702 of an overhead storage bin 704 is illustrated, in accordance with an exemplary embodiment. The overhead storage bin 704 may be analogous to the overhead storage bin 108 of the aircraft cabin 100. The multiple views of the aircraft sanitization system 700 may include a perspective view 706a, a front view 706b, a front view 706c of the handle 702, a bottom view 706d of the handle 702, and a side view 706e. The aircraft sanitization device 700 may include a curved enclosure 708 operatively coupled to a first surface 710 of an enclosed area, which is the overhead storage bin 704 in this case. At a first position, the curved enclosure 708 at least partially encloses the handle 702 affixed to the first surface 710. The first position is illustrated in each of the perspective view 706a, the front view 706b, the front view 706c of the handle 702, the bottom view 706d of the handle, and the side view 706e. Further, the handle 702 may enable access to the enclosed area. Further, the curved enclosure 708 may include an inner surface 712 facing the first surface 710 at the first position of the curved enclosure 708. Additionally, the curved enclosure 708 may include an outer surface 714 facing away from the first surface 710 at the first position.

The aircraft sanitization device 700 may also include a set of UV LEDs 716 affixed to the inner surface 712. It may be noted that the set of UV LEDs 716 may be configured to sanitize the handle 702. In some embodiments, the set of UV LEDs 716 may include at least one UV-C LED. Further, the aircraft sanitization device 700 may include at least one switch placed on at least one of the first surface 710 and a second surface (not shown in FIG. 7) of the enclosed area. It may be noted that each of the at least one switch is activated in a closed state of the enclosed area and each of the at least one switch is deactivated in an open state of the enclosed area. Further, the aircraft sanitization device 700 may include at least one locking mechanism (not shown in FIG. 7). The at least one locking mechanism may be configured to engage with the first surface 710 in the closed state and disengage with the first surface 710 in the open state. Further, the aircraft sanitization device 700 may include a controller communicatively coupled to each of the set of UV LEDs 716, the at least one switch, and the at least one locking mechanism. The controller may be configured to activate the set of UV LEDs 716, when each of the at least one switch is activated and the locking mechanism engages the first surface 710 in the closed state.

The aircraft sanitization device 700 may further include at least one sensor (not shown in FIG. 7) affixed to the inner surface 712 of the curved enclosure 708 and configured to generate a deactivation signal based on a predefined criterion. By way of an example, the predefined criterion may include detection of a body part of a user. It may be noted that the controller may be communicatively coupled to the at least one sensor. It may also be noted that the controller may be further configured to deactivate the set of UV LEDs 716 based on the deactivation signal generated by the at least one sensor. In an embodiment, the set of UV LEDs 716 may be affixed to the first surface 710 and may be configured to sanitize the inner surface 712 of the curved enclosure 708. In another embodiment, the curved enclosure 708 may be equivalent to the handle 702 of the overhead storage bin 704. It will be apparent to a person skilled in the art that the aircraft sanitization device 700 may not be limited to an aircraft and may be implemented in trains, buses, cars, trucks, or any vehicle thereof. The aircraft sanitization device 700 may also be implemented in public use areas, for example, cinema halls, malls, etc.

Figure 8:
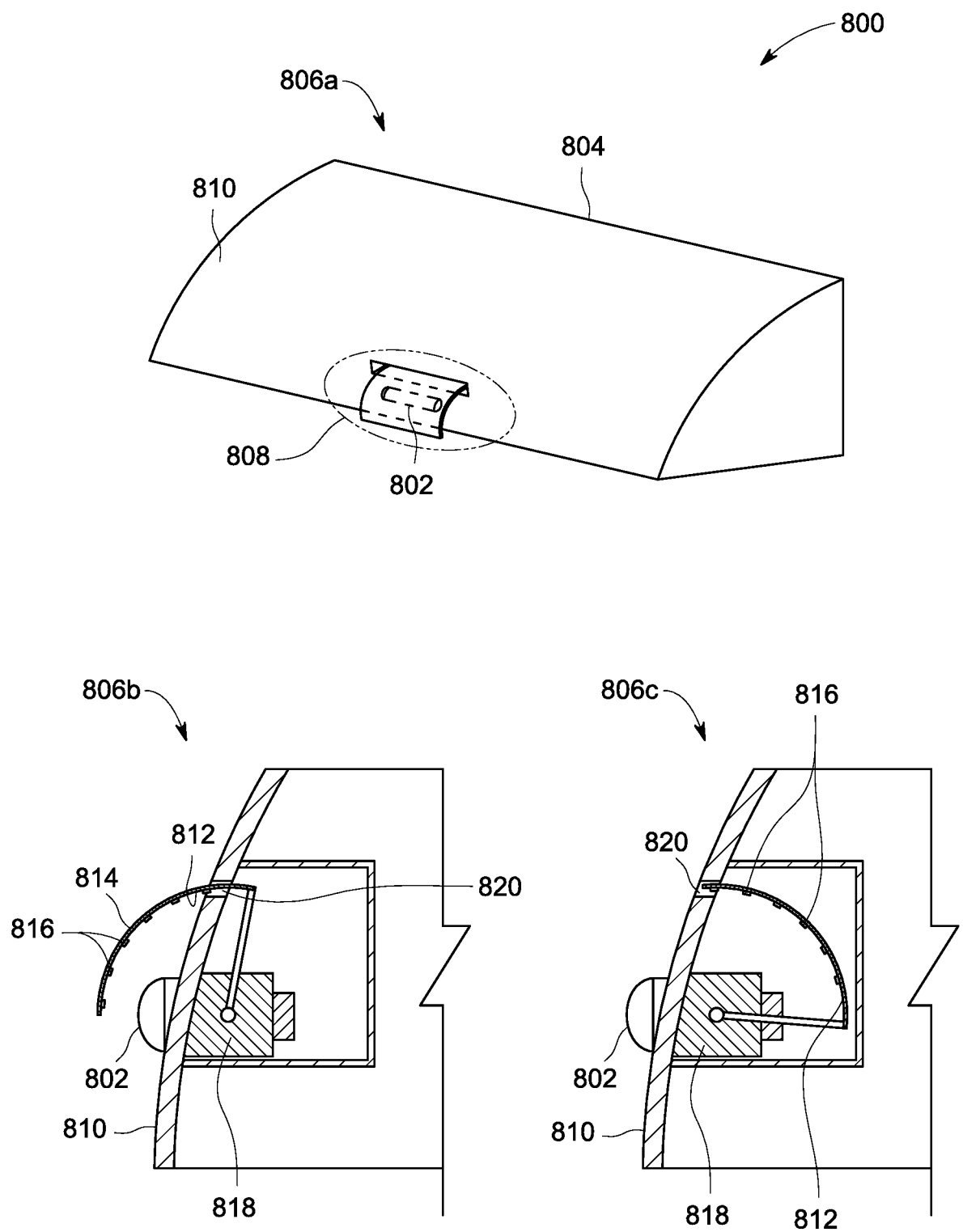
FIG. 8 illustrates multiple views of an aircraft sanitization device for sanitizing a handle of an overhead storage bin, in accordance with another exemplary embodiment.

Referring now to FIG. 8, multiple views of an aircraft sanitization device 800 for sanitizing a handle 802 of an overhead storage bin 804 is illustrated, in accordance with an another exemplary embodiment. The overhead storage bin 804 may be analogous to the overhead storage bin 108 of the aircraft cabin 100. The multiple views of the aircraft sanitization system 800 include a perspective view 806a, a side view 806b, and a side view 806c. The aircraft sanitization device 800 may include a curved enclosure 808 operatively coupled to a first surface 810 of an enclosed area, which is the overhead storage bin 804 in this case. At a first position, the curved enclosure 808 at least partially encloses the handle 802 affixed to the first surface 810, which may enable access to the enclosed area. In this exemplary embodiment, the curved enclosure 908 remains in the first position only. The first position is illustrated in the side view 806b. Further, the curved enclosure 808 may include an inner surface 812 facing the first surface 810 at the first position of the curved enclosure 808. The curved enclosure 808 may also include an outer surface 814 facing away from the first surface 810 at the first position.

The aircraft sanitization device 800 may include a set of UV LEDs 816 affixed to the inner surface 812. It may be noted that the set of UV LEDs 816 may be configured to sanitize the handle 802. In some embodiments, the set of UV LEDs 816 may include at least one UV-C LED. The aircraft sanitization device 800 may also include at least one switch (not shown in FIG. 8) placed on at least one of the first surface 810 and a second surface of the enclosed area. It may be noted that each of the at least one switch is activated in a closed state of the enclosed area and each of the at least one switch is deactivated in an open state of the enclosed area. The closed state is illustrated in the side view 806b and the open state is illustrated in the side view 806c.

The aircraft sanitization device 800 may also include at least one locking mechanism (not shown in FIG. 8). The at least one locking mechanism may be configured to engage with the first surface 810 in the closed state and disengage with the first surface 810 in the open state. The aircraft sanitization device 800 may include a controller communicatively coupled to each of the set of UV LEDs 816, the at least one switch, and the at least one locking mechanism. The controller may be configured to activate the set of UV LEDs 816, when each of the at least one switch is activated and the locking mechanism engages the first surface 810 in the closed state.

In order to move the curved enclosure 808 from the first position to at least one of a second position and at least one intermediate position, the aircraft sanitization device 800 may include a rotating mechanism 818 that may be operatively coupled to the curved enclosure 808 and may be configured to move the curved enclosure 808. The rotating mechanism 818 is illustrated in each of the side view 806b and the side view 806c. At the second position, the curved enclosure 808 completely discloses the handle 802 and at each of the at least one intermediate position, the curved enclosure 808 partially discloses the handle 802. In an embodiment, the first surface 810 of the enclosed area may include a slit 820 to enable movement of the curved enclosure 808 through the first surface 810 between the first position, the second position, and at least one intermediate position. The slit 820 is illustrated in each of the side view 806b and the side view 806c. It may be noted the controller may be communicatively coupled to the rotating mechanism. Further, the controller may be configured to instruct the rotating mechanism 818 to move the curved enclosure 808 to the first position, when each of the at least one switch is activated and the locking mechanism engages the first surface 810 in the closed state. Additionally, the controller may configured to instruct the rotating mechanism 818 to move the curved enclosure 808 to one of the second position and the at least one intermediate position, when at least one of the at least one switch is deactivated and the locking mechanism disengages the first surface 810.

The aircraft sanitization device 800 may further include at least one sensor affixed to the inner surface 812 of the curved enclosure 808 and may be configured to generate a deactivation signal based on a predefined criterion. By way of an example, the predefined criterion may include detection of a body part of a user. It may be noted that the controller may be communicatively coupled to the at least one sensor. It may also be noted that the controller may further be configured to deactivate the set of UV LEDs 816 based on the deactivation signal generated by the at least one sensor. It will be apparent to a person skilled in the art that the aircraft sanitization device 800 may not be limited to an aircraft and may be implemented in trains, buses, cars, trucks, or any vehicle thereof. The aircraft sanitization device 800 may also be implemented in public use areas, for example, cinema halls, malls, etc.

Figure 9:
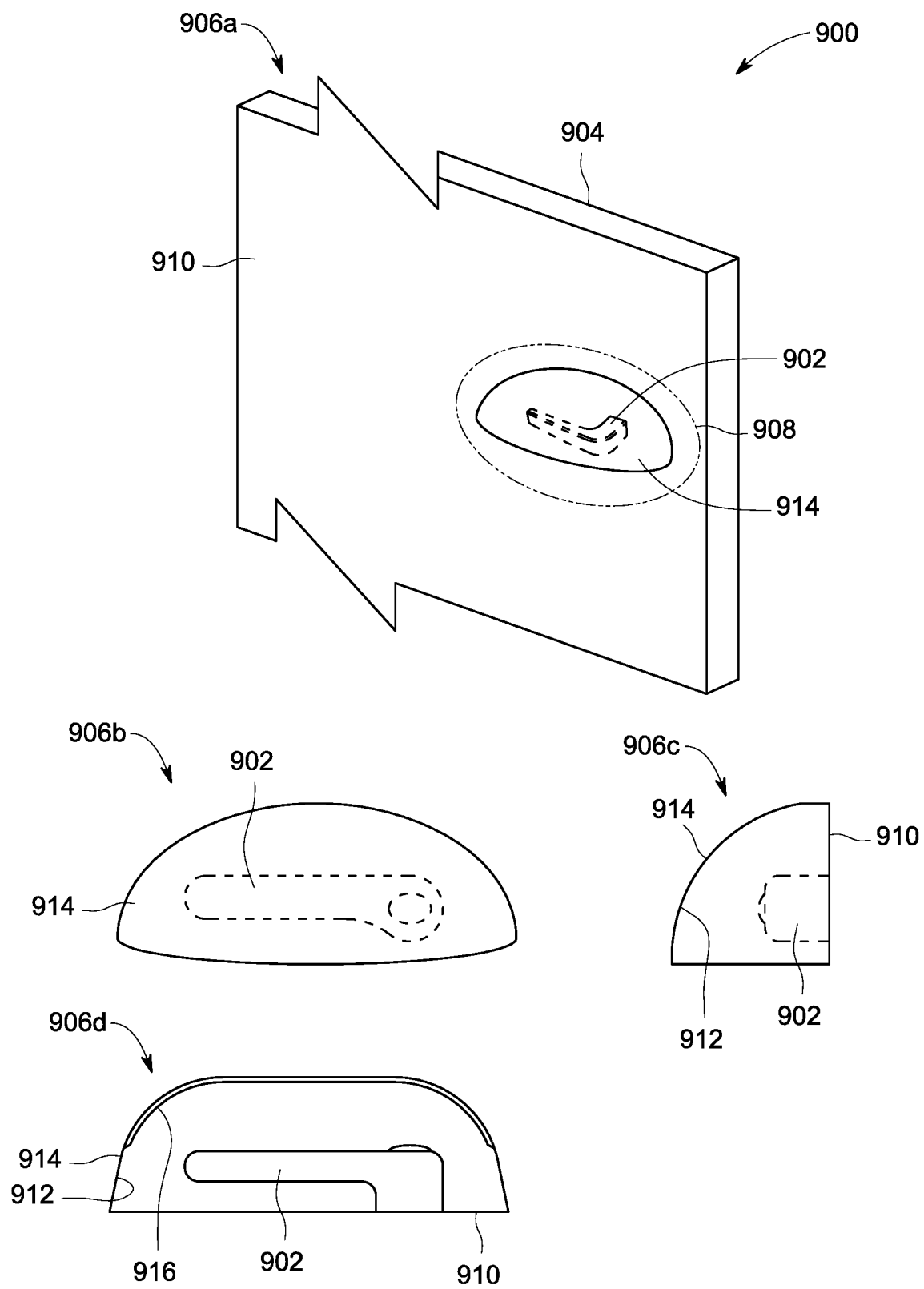
FIG. 9 illustrates multiple views of an aircraft sanitization device for sanitizing a handle of a closed compartment, in accordance with an exemplary embodiment.

Referring now to FIG. 9, multiple views of a sanitization device 900 for sanitizing a handle 902 is illustrated, in accordance with an exemplary embodiment. The handle 902 may be affixed to a door 904, which may be used to open or close an enclosed area such as a lavatory (for example, the lavatory 110 of the aircraft cabin 100), an exit, an emergency exit, a cockpit, a galley, or the like. The multiple views of the aircraft sanitization system 900 may include a perspective view 906a, a front view 906b, a side view 906c, and a bottom view 906d. The aircraft sanitization device 900 may include a curved enclosure 908 operatively coupled to a first surface 910 of the enclosed area. The first surface 910 is illustrated in each of the perspective view 906a, the side view 906c, and the bottom view 906d. At a first position, the curved enclosure 908 at least partially encloses the handle 902 affixed to the first surface 910. In this exemplary embodiment, the curved enclosure 908 remains in the first position only. The handle 902 may enable access to the enclosed area. Further, the curved enclosure 908 may include an inner surface 912 facing the first surface 910 at the first position of the curved enclosure 908 and an outer surface 914 facing away from the first surface 910 at the first position.

The aircraft sanitization device 900 may further include a set of UV LEDs 916 affixed to the inner surface 912. It may be noted that the set of UV LEDs 916 may be configured to sanitize the handle 902. In some embodiments, the set of UV LEDs 916 may include at least one UV-C LED. The set of UV LEDs 916 is illustrated in the bottom view 906d. Further, the aircraft sanitization device 900 may include at least one switch (not shown in FIG. 9) placed on at least one of the first surface 910 and a second surface of the enclosed area. It may be noted that each of the at least one switch is activated in a closed state of the enclosed area and each of the at least one switch is deactivated in an open state of the enclosed area. By way of an example, when the enclosed area is a lavatory, a switch may be located, such that, on closure of the door of the lavatory the switch is activated and upon opening the door the switch is deactivated.

The aircraft sanitization device 900 may additionally include at least one locking mechanism (not shown in FIG.

9). The at least one locking mechanism may be configured to engage with the first surface 910 in the closed state and disengage with the first surface 910 in the open state. By way of an example, when the enclosed area is a lavatory, a locking mechanism may be a sliding latch that may be slid in one horizontal direction to close the door and in the opposite horizontal direction to open the door. The aircraft sanitization device 900 may also include a controller that may be communicatively coupled to each of the set of UV LEDs 916, the at least one switch, and the at least one locking mechanism. The controller may be configured to activate the set of UV LEDs 916, when each of the at least one switch is activated and the locking mechanism engages the first surface 910 in the closed state.

The aircraft sanitization device 900 may further include at least one sensor affixed to the inner surface 912 of the curved enclosure 908 and may be configured to generate a deactivation signal based on a predefined criterion. By way of an example, the predefined criterion may include detection of a body part of a user. It may be noted that the controller may be communicatively coupled to the at least one sensor. It may also be noted that the controller may be further configured to deactivate the set of UV LEDs 916 based on the deactivation signal generated by the at least one sensor. It will be apparent to a person skilled in the art that the aircraft sanitization device 900 may not be limited to an aircraft and may be implemented in trains, buses, cars, trucks, or any vehicle thereof. The aircraft sanitization device 900 may also be implemented in public use areas, for example, cinema halls, malls, etc.

Figure 10:
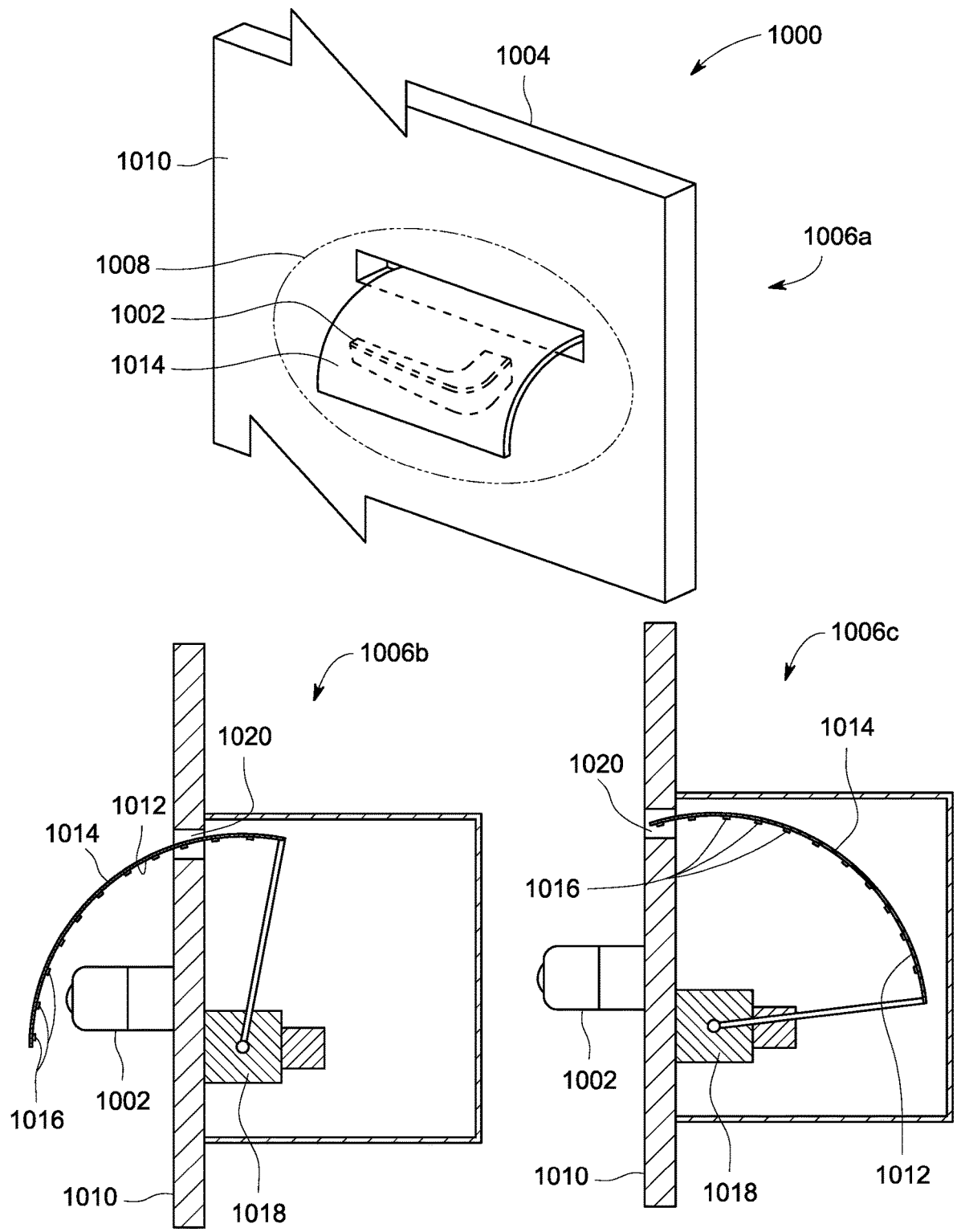
FIG. 10 illustrates multiple views of an aircraft sanitization device for sanitizing a handle of a closed compartment, in accordance with another exemplary embodiment.

Referring now to FIG. 10, multiple views of an aircraft sanitization device 1000 for sanitizing a handle 1002 is illustrated, in accordance with an exemplary embodiment. The handle 1002 may be affixed to a door 1004. The door may be configured to open or close an enclosed area such as a lavatory (for example, the lavatory 110 of the aircraft cabin 100), an exit, an emergency exit, a cockpit, a galley, or the like. The multiple views of the aircraft sanitization system 1000 may include a perspective view 1006a, a side view 1006b, and a side view 1006c. The aircraft sanitization device 1000 may include a curved enclosure 1008 operatively coupled to a first surface 1010 of the enclosed area. At a first position, the curved enclosure 808 may at least partially enclose the handle 1002 affixed to the first surface 1010, which enable access to the enclosed area. The first position is illustrated in the side view 1006b. The curved enclosure 1008 may include an inner surface 1012 facing the first surface 1010 at the first position of the curved enclosure 1008 and an outer surface 1014 facing away from the first surface 1010 at the first position.

The aircraft sanitization device 1000 may include a set of UV LEDs 1016 affixed to the inner surface 1012. It may be noted that the set of UV LEDs 1016 may be configured to sanitize the handle 1002. In some embodiments, the set of UV LEDs 1016 may include at least one UV-C LED. The inner surface 1012 and the set of UV LEDs 1016 are illustrated in each of the side view 1006b and the side view 1006c. The aircraft sanitization device 1000 may include at least one switch placed on at least one of the first surface 1010 and a second surface of the enclosed area. It may be noted that each of the at least one switch is activated in a closed state of the enclosed area and each of the at least one switch is deactivated in an open state of the enclosed area. By way of an example, when the enclosed area is a lavatory, a switch may be located, such that, on closure of the door of the lavatory the switch is activated and upon opening the door the switch is deactivated. The closed state is illustrated in the side view 1006b and the open state is illustrated in the side view 1006c. The aircraft sanitization device 1000 may include at least one locking mechanism. The at least one locking mechanism may be configured to engage with the first surface 1010 in the closed state and disengage with the first surface 1010 in the open state. By way of an example, when the enclosed area is a lavatory, a locking mechanism may be a sliding latch that may be slid in one horizontal direction to close the door and in the opposite horizontal direction to open the door. Further, the aircraft sanitization device 1000 may include a controller (not shown in FIG. 10) communicatively coupled to each of the set of UV LEDs 1016, the at least one switch, and the at least one locking mechanism. The controller may be configured to activate the set of UV LEDs 1016, when each of the at least one switch is activated and the locking mechanism engages the first surface 1010 in the closed state.

The aircraft sanitization device 1000 may further include a rotating mechanism 1018 operatively coupled to the curved enclosure 1008 and configured to move the curved enclosure 1008 from the first position to at least one of a second position and at least one intermediate position. The rotating mechanism 1018 is illustrated in each of the side view 1006b and the side view 1006c. At the second position, the curved enclosure 1008 completely discloses the handle 1002 and at each of the at least one intermediate position the curved enclosure 1008 partially discloses the handle 1002. In an embodiment, the first surface 1010 of the enclosed area may include a slit 1020 to enable movement of the curved enclosure 1008 through the first surface 1010 between the first position, the second position, and at least one intermediate position. The slit 1020 is illustrated in each of the side view 1006b and the side view 1006c. The movement of the curved enclosure 1008 may be through the rotating mechanism 1018.

The controller may be communicatively coupled to the rotating mechanism 1018 and may be configured to instruct the rotating mechanism 1018 to move the curved enclosure 1008 to the first position, when each of the at least one switch is activated and the locking mechanism engages the first surface 1010 in the closed state. In contrast, the controller may configured to instruct the rotating mechanism 1010 to move the curved enclosure 1008 to one of the second position and the at least one intermediate position, when at least one of the at least one switch is deactivated and the locking mechanism disengages the first surface 1010.

The aircraft sanitization device 1000 may include at least one sensor affixed to the inner surface 1012 of the curved enclosure 1008 and may be configured to generate a deactivation signal based on a predefined criterion. By way of an example, the predefined criterion may include detection of a body part of a user. It may be noted that the controller may be communicatively coupled to the at least one sensor. It may also be noted that the controller may be further configured to deactivate the set of UV LEDs 1016 based on the deactivation signal generated by the at least one sensor. It will be apparent to a person skilled in the art that the aircraft sanitization device 1000 may not be limited to an aircraft and may be implemented in trains, buses, cars, trucks, or any vehicle thereof. The aircraft sanitization device 1000 may also be implemented in public use areas, for example, cinema halls, malls, etc.

As will further be appreciated by those skilled in the art, current sanitization systems lack the mechanism to effectively sanitize surfaces in an aircraft with passengers and crew members on board. The techniques described above provide for sanitizing surfaces in an aircraft. In particular, the above techniques provide for sanitizing surfaces in an aircraft through a plurality of sets of UV LEDs. Surfaces such as a tray, a lavatory door handle, or an overhead storage bin handle may be sanitized with passengers and crew members on board using the above techniques. The techniques provide for effective means of preventing UV light radiations from contacting a body part of a user. Surfaces such as locking portions of safety belts may be sanitized before or after a flight in absence of passengers and crew members. The techniques provide enclosures such as stowage encasings for storing the locking portions of safety belts, frames and pockets for storing trays, and curved enclosures for covering handles. Each of the plurality of sets of UV LEDs is affixed inside such enclosures. Further, the techniques employ sensors to detect presence of the body part of the user within the enclosures. The sensors activate the UV LEDs in closed or locked states of the surfaces to prevent the UV light radiations from contacting the body part of the user. The above mentioned techniques may be used in conjunction with existing state of the art techniques employing UV LEDs for sanitizing air released from air ducts of air conditioning systems in the aircraft, interiors of the lavatory, interiors of aircraft cabin, hand-held devices (for example, in-flight entertainment controllers), and the like.

The specification has described aircraft sanitization systems and devices. The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. An aircraft sanitization system comprising:
   a safety belt comprising a first portion affixed to a first fabric part of the safety belt and a second portion affixed to a second fabric part of the safety belt, wherein the first portion is configured to receive the second portion for fastening the safety belt;
   a first stowage encasing configured to completely enclose the first portion, wherein the first stowage encasing comprises:
      a first inner wall configured to surround an outer surface of the first portion;
      a first set of Ultraviolet (UV) Light Emitting Diodes (LEDs) affixed to the first inner wall and configured to sanitize the outer surface of the first portion;
      a tongue configured to cooperate with the first portion of the safety belt; and
      a second set of UV LEDs attached on a surface of the tongue and configured to sanitize an inner surface of the first portion; and
   a second stowage encasing configured to enclose the second portion, wherein the second stowage encasing comprises:
      a second inner wall configured to surround the second portion; and
      a third set of UV LEDs affixed to the second inner wall and configured to sanitize the second portion.

2. The aircraft sanitization system of claim 1, wherein:
   the first stowage encasing further comprises a first slit configured to receive the first fabric part, and wherein the first slit comprises:
      a first pair of rollers cooperating with the first fabric part, wherein the first pair of rollers enable the first stowage encasing to slide over the first fabric part to enclose the first portion, and wherein the first fabric part passes through the first stowage encasing via the first slit; and
   the second stowage encasing further comprises a second slit configured to receive the second fabric part, and wherein the second slit comprises:
      a second pair of rollers cooperating with the second fabric part, wherein the second pair of rollers enable the second stowage encasing to slide over the second fabric part to enclose the second portion, and wherein the second fabric part passes through the second stowage encasing via the second slit.

3. The aircraft sanitization system of claim 2, wherein:
   the first stowage encasing further comprises a first motorized mechanism coupled to the first pair of rollers, and wherein the first motorized mechanism is configured to activate the first pair of rollers to slide the first stowage encasing over the first fabric part; and
   the second stowage encasing further comprises a second motorized mechanism coupled to the second pair of rollers, and wherein the second motorized mechanism is configured to activate the second pair of rollers to slide the second stowage encasing over the second fabric part.

4. The aircraft sanitization system of claim 3, further comprising:
   a first set of sensors within the first stowage encasing, wherein the first set of sensors is configured to determine complete enclosure of the first portion by the first stowage encasing;
   a second set of sensors within the second stowage encasing, wherein the second set of sensors is configured to determine complete enclosure of the second portion by the second stowage encasing; and
   a controller communicatively coupled to each of the first set of UV LEDs, the second set of UV LEDs, the third set of UV LEDs, the first set of sensors, the second set of sensors, the first motorized mechanism, and the second motorized mechanism, wherein the controller is configured to:

instruct the first motorized mechanism to slide over the first fabric part to enclose the first stowage encasing, in response to a sanitization activation signal;

instruct the second motorized mechanism to slide over the second fabric part to enclose the second stowage encasing, in response to the sanitization activation signal;

activate each of the first set of UV LEDs and the second set of UV LEDs in response to the first set of sensors establishing complete enclosure of the first portion by the first stowage encasing; and activate the third set of UV LEDs in response to the second set of sensors establishing complete enclosure of the second portion by the second stowage encasing.

5. The method of claim 4, wherein the controller is further configured to:

instruct the first motorized mechanism to slide over the first fabric part to reveal the first stowage encasing after expiry of a predefined time period; and instruct the second motorized mechanism to slide over the second fabric part to reveal the second stowage encasing after expiry of the predefined time period.

6. The method of claim 4, wherein the controller is further configured to:

deactivate each of the first set of UV LEDs and the second set of UV LEDs in response to the first set of sensors establishing partial enclosure of the first portion by the first stowage encasing; and deactivate the third set of UV LEDs in response to the second set of sensors establishing partial enclosure of the second portion by the second stowage encasing.

* * * * *